United States Patent [19]
Field et al.

[11] Patent Number: 5,557,104
[45] Date of Patent: Sep. 17, 1996

[54] METHOD AND APPARATUS FOR DETERMINING CRYSTALLOGRAPHIC CHARACTERISTICS IN RESPONSE TO CONFIDENCE FACTORS

[75] Inventors: David P. Field, Pleasant Grove; David J. Dingley, Provo, both of Utah

[73] Assignee: Texsem Laboratories, Inc., Provo, Utah

[21] Appl. No.: 547,299

[22] Filed: Oct. 24, 1995

[51] Int. Cl.$^6$ .................................................. G01N 23/203
[52] U.S. Cl. ........................ 250/307; 250/306; 250/310
[58] Field of Search .................................. 250/307, 306, 250/310, 311

[56] References Cited

U.S. PATENT DOCUMENTS

| | | | |
|---|---|---|---|
| 4,990,779 | 2/1991 | Yochitori et al. | 250/307 |
| 5,466,934 | 11/1995 | Adams et al. | 250/307 |

OTHER PUBLICATIONS

Orientation Imaging: The Emergence of a New Microscopy, Adams et al. Metallurgical Transactions A vol. 24A, Apr. 1993, pp. 819–831.

Individual Lattice Orientation Measurements Development and Application of a Fully Automatic Technique. Doctoral Dissertation by Stuart Wright; pp. 33–35 May 1992.

*Primary Examiner*—Jack I. Berman
*Assistant Examiner*—Kiet T. Nguyen
*Attorney, Agent, or Firm*—Meschkow & Gresham

[57] ABSTRACT

An apparatus for determining the reliability of crystallographic solutions of a specimen includes an electron beam generator, a stage for holding the specimen, an image collection system for obtaining diffraction images of crystals within the specimen, and processor for processing the diffraction images to obtain most probable indexing solutions for the crystals and to generate confidence factors associated with the most probable indexing solutions. The apparatus may utilize the confidence factors to determine the phase of the crystals within the specimen. The confidence factors may also be incorporated into reports representing the statistical confidence of various crystallographic characteristics of the specimen.

23 Claims, 5 Drawing Sheets

METHOD AND APPARATUS FOR DETERMINING CRYSTALLOGRAPHIC CHARACTERISTICS IN RESPONSE TO CONFIDENCE FACTORS

TECHNICAL FIELD OF THE INVENTION

The present invention is related in general to material sciences. In particular, the present invention is related to the determination of crystallographic characteristics of a crystalline specimen utilizing diffraction patterns obtained from an electron microscope.

BACKGROUND OF THE INVENTION

The properties and characteristics of a polycrystalline material are partially determined by the size and shape of the constituent crystals or grains, the orientation of the crystal lattices, and the spatial location of the crystals. Accordingly, these attributes of the material microstructure must be determined in order to understand why certain materials behave as they do, to predict how other materials will behave, and to alter or otherwise control material forming and processing techniques to improve specific material properties.

Crystal lattice planes are typically identified by a procedure known as crystal indexing. Automated crystal indexing procedures have enabled researchers, material processors, and manufacturers to obtain valuable microstructure information over a relatively large material specimen area. Generally, such a procedure repetitively bombards selected points of a material specimen with a beam of electrons. The electrons interact with a small volume of the material sample at the selected points, and diffracting crystals cause electron backscatter diffraction patterns (EBSPs) to form on a phosphor screen near the specimen. The EBSPs may be imaged through a video camera and digitized for further processing.

Good quality EBSPs include a number of intersecting, relatively high intensity bands that are usually referred to as Kikuchi bands. The Kikuchi bands result from electrons being diffracted from various planes in the crystal lattice at the point of bombardment. An abundance of microstructure information, including the crystal indexing solution, may be obtained by analyzing the various parameters of the Kikuchi bands. Computer-implemented image processing techniques have been developed to analyze Kikuchi bands from EBSPs taken at numerous points on a material sample and to generate displays of the specimen that convey a wealth of microstructure information.

A conventional processing technique utilizes a computational iteration scheme to determine the resultant crystal indexing solution. The indexing solution is calculated a number of times using different computational parameters, and a voting algorithm selects the "best" solution. Unfortunately, this algorithm does little more than rank the different solutions, and no probabilistic measurements or statistical confidence data is included in the analysis. Thus, one must rely on the selected indexing solution without knowing how reliable the data may actually be. Unfortunately, any further analyses or calculations based on an unreliable indexing solution will also be unreliable, and a reviewer may not know that the results are unreliable.

Although there are only seven basic crystal types, there are approximately 40,000 different crystal phase variations. If known, the crystal phase of a material provides structural parameters and geometrical relationships necessary for the determination of other material properties. Thus, the crystal phase is an important characteristic of a material that can be valuable to researchers and scientists. For example, a crystal phase identity is typically assumed when performing crystal indexing processes. Given the identity of the crystal phase, mathematical relationships required to calculate the crystal indices are selected. However, many polycrystalline materials have more than one distinct crystal phase. In addition, other materials may have an unknown phase or an unknown combination of phases. Thus, an indexing solution for such a material may be incomplete or erroneous without a proper identification of the crystal phase or phases within the particular specimen.

SUMMARY OF THE INVENTION

Accordingly, it is an advantage of the present invention that an improved method and apparatus for indexing a crystalline material is provided.

In addition, it is an advantage of the present invention that an improved method and apparatus for determining the crystal phase of a specimen is provided.

Another advantage is that the present invention provides reliability data associated with an indexing solution for a crystal.

A further advantage is that the present invention is capable of determining an indexing solution for a crystal without the precise knowledge of the crystal phase.

Another advantage is that an indexing solution may be obtained for a specimen having multiple crystal phases.

The above and other advantages of the present invention are carried out in one form by a method for indexing a crystal lattice plane of a specimen. The method involves obtaining a plurality of indexing solutions for a crystal within the specimen, selecting a most probable solution from the plurality of indexing solutions, generating a confidence factor for the most probable solution, and producing a report associated with the crystal.

BRIEF SUMMARY OF THE FIGURES

A more complete understanding of the present invention may be derived by referring to the detailed description and claims when considered in connection with the Figures, wherein like reference numbers refer to similar items throughout the Figures, and:

DETAILED DESCRIPTION OF THE PREFERRED EMBODIMENT

Figure 1:
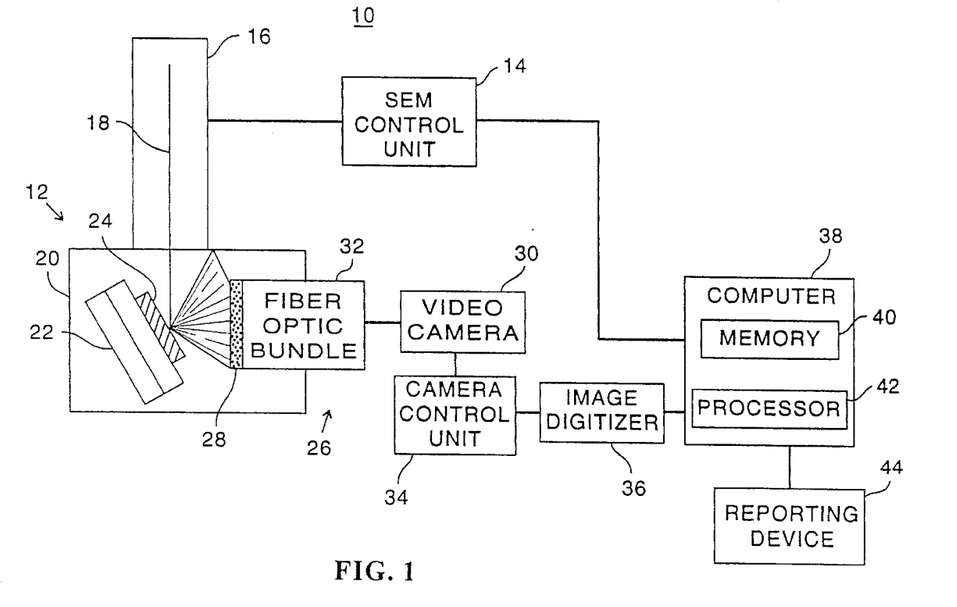
FIG. 1 shows a block diagram of an apparatus according to the present invention.

FIG. 1 is a block diagram of an apparatus 10 for indexing crystal lattice planes of a specimen. Apparatus 10 is also configured to determine the reliability of the indexing solution. According to the preferred embodiment, apparatus 10 incorporates a conventional scanning electron microscope (SEM) 12. However, those skilled in this art will recognize that apparatus 10 may utilize a transmission electron microscope depending upon the specific application. SEM 12 includes a SEM control unit 14 that controls an electron beam generator 16. Under the direction of SEM control unit 14, electron beam generator 16 discharges a focused electron beam 18 into a vacuum chamber 20. A holding stage 22 is mounted in vacuum chamber 20 such that a material specimen 24 mounted thereon is bombarded or illuminated by electron beam 18.

An image collection system 26 is utilized to collect images of backscattered electrons diffracted from specimen 24. Image collection system 26 includes a screen 28 that is coated with a scintillating material such as phosphorus. Screen 28 is coupled to a video camera 30 through a fiber optic bundle 32. Screen 28 luminesces in accordance with the pattern of diffracted electrons falling thereon. The resulting electron backscatter diffraction patterns (EBSPs) are captured by video camera 30, where they are converted to electronic signals, passed through a camera control unit 34, and converted into digital data in an image digitizer 36.

A computer 38 controls the determination of the crystal indexing solution of specimen 24 and the reliability of the solution. Computer 38 is a conventional computer desirably having as much computing power as is economically practical. Computer 38 includes conventional computer components, including a memory 40 and a processor 42. Memory 40 stores programming instructions that define various processes carried out by processor 42 and other components of apparatus 10. In addition, memory 40 stores data generated by the operation of apparatus 10.

Computer 38 controls the movement of holding stage 22, preferably via SEM control unit 14. Through control of holding stage 22 and electronic steering of electron beam 18, a wide area of specimen 24 may be illuminated by electron beam 18 with backscattered electrons falling upon screen 28. Computer 38 may be coupled to a reporting device 44 that produces a report associated with the crystals within specimen 24. For purposes of this description, a report may include a crystal orientation image, a crystal phase map, a specimen grain size map, a statistical map representing the reliability or confidence of crystallographic data accumulated for specimen 24, or other reports describing crystallographic characteristics. Reporting device 44 may be a video display terminal, a printer, or other device which may serve to convey information related to the crystals within specimen 24.

Figure 2:
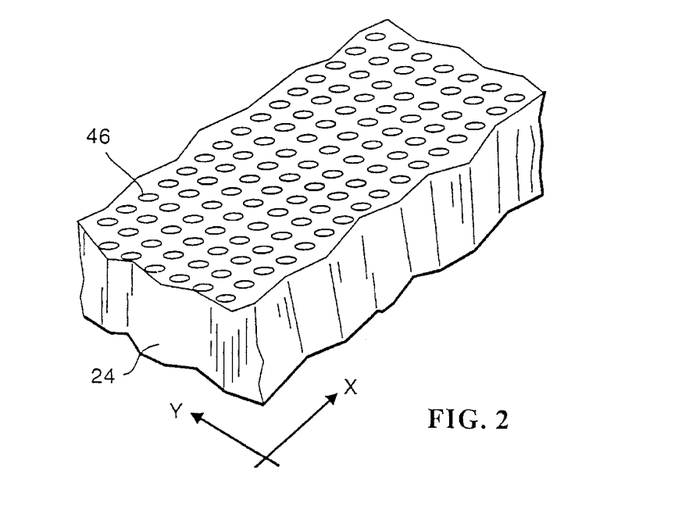
FIG. 2 shows a schematic representation of a portion of a specimen ready for scanning by the apparatus.

FIG. 2 shows a perspective schematic view of an exemplary portion of specimen 24. FIG. 2 illustrates numerous points 46 upon specimen 24. Points 46 indicate the locations upon specimen 24 that are bombarded with electron beam 18 (see FIG. 1). Points 46 may or may not be noticeable on specimen 24 after completion of scanning. An EBSP image is collected from each point 46, as discussed below. Each point 46 represents a small volume of specimen 24, preferably smaller than an average crystallite.

FIG. 2 illustrates points 46 as forming an array with aligned rows and columns, which is a convenient but otherwise unnecessary arrangement for points 46. The spacing between points 46 may vary from application to application, and is desirably a parameter that may be set by an operator prior to scanning specimen 24. An (x,y) coordinate system may be utilized to indicate the relative spatial locations of points 46. Processor 42 and memory 40 cooperate to control the scanning operation and to store data associated with points 46.

Figure 3:
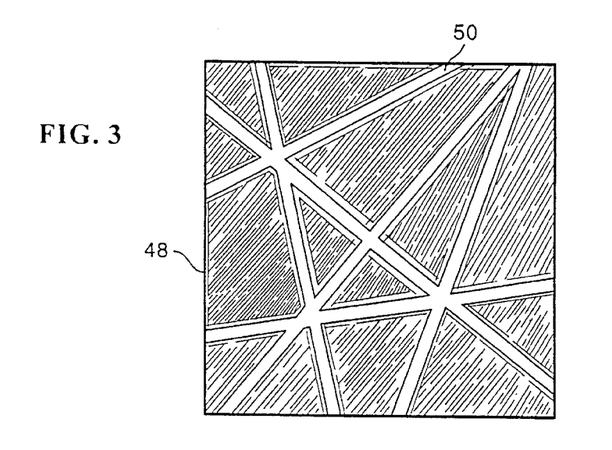
FIG. 3 shows a schematic representation of an exemplary electron backscatter diffraction pattern obtained by the apparatus.

With reference to FIG. 3, a schematic view of an exemplary EBSP 48 is shown. Apparatus 10 preferably collects at least one EBSP for each point 46 illuminated during scanning of specimen 24. EBSP 48 includes a plurality of bands 50 (typically referred to as Kikuchi bands) formed by the diffraction of electron beam 18. Kikuchi bands 50 intersect each other at various points and are generally bordered by thin lines of lower intensity. FIG. 3 exaggerates the contrast available in a typical EBSP for the sake of clarity. The preferred embodiment analyzes Kikuchi bands 50 to obtain indexing solutions for the crystals associated with points 46.

Generally, apparatus 10 determines the indexing solution for a crystal within specimen 24 by collecting and processing an EBSP associated with the crystal. The indexing solution is computed a number of times by analyzing different groups of Kikuchi bands, and an algorithm is performed to select a statistically preferred solution. Apparatus 10 subsequently determines the reliability or confidence of the selected solution and generates a confidence factor (CF) for the selected solution. The CF may be utilized to determine the crystal phase of specimen 24, or it may be represented in a crystal orientation map, a statistical map, or other data report.

Figure 4:
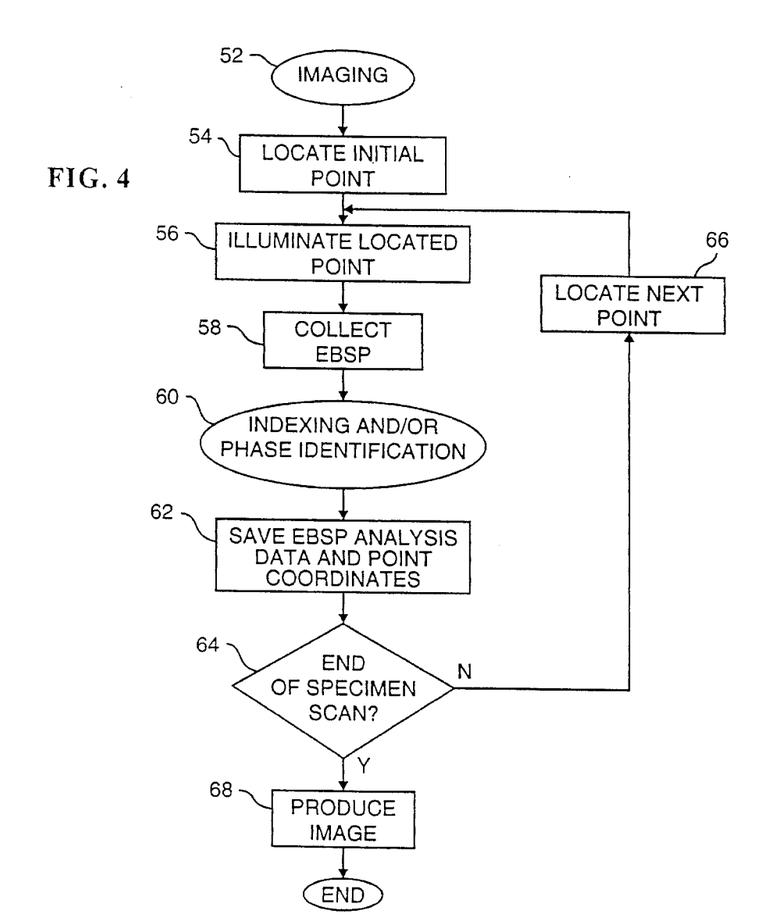
FIG. 4 is a flow diagram of an imaging process performed by the apparatus.

With reference now to FIG. 4, an imaging process 52 performed by apparatus 10 is depicted as a flow diagram. Process 52 is performed after specimen 24 is prepared according to conventional SEM procedures and mounted on holding stage 22. After mounting on holding stage 22, specimen 24 is not moved relative to holding stage 22 until scanning is complete so that a common coordinate system may be used for all points 46 (see FIG. 2). Process 52 begins with a task 54, which locates an initial point 46 for illumination by electron beam 18. SEM control unit 14, under the control of computer 38, regulates the movement of holding stage 22 and the steering of electron beam ]8 such that electron beam 18 illuminates specimen 24 at the desired location. As stated above, electron beam 18 is preferably focused to illuminate a volume within a single crystal at each point 46. Following task 54, a task 56 causes SEM 12 to illuminate specimen 24 with electron beam 18. Upon illumination, a crystal within specimen 24 diffracts electron beam 18 at specific angles. As shown in FIG. 1, diffracted electrons that react with the crystal impinge upon screen 28 to create an EBSP.

After task 56, a task 58 collects an EBSP of the crystal associated with the illuminated point 46 (see FIG. 3). Image collection system 26 preferably collects a visual representation of the EBSP, which is eventually digitized by image digitizer 36 for further processing by computer 38. Thus, for each point 46, electron beam 18 illuminates specimen 24 for at least a length of time necessary to allow computer 38 to receive a digital representation of the EBSP. Following task 58, a procedure 60 is initiated.

Procedure 60 encompasses several processes, which are described below. Generally, procedure 60 determines an indexing solution for the particular crystal, computes a statistical indication of the reliability of the indexing solution, and/or determines the crystal phase at the current point 46. Procedure 60 analyzes the current EBSP, determines various crystallographic characteristics at the particular point 46, and computes confidence data related to the crystallographic characteristics. Following procedure 60, a task 62 saves the EBSP analysis data and the spatial coordinates of the current illuminated point 46 for later use by apparatus 10. The spatial coordinates may be used to generate images, maps, or other reports of specimen 24 (described below) that show the relative locations of the crystals within specimen 24.

Figure 5:
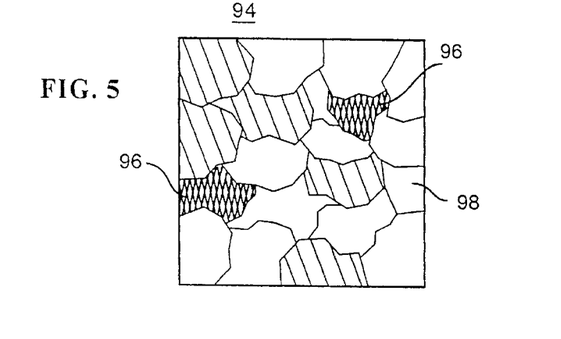
FIG. 5 shows a schematic representation of an exemplary crystal image produced by the apparatus.

After task 62, a query task 64 tests whether imaging process 52 is at the end of the specimen scan. If more points 46 remain to be scanned, then a task 66 locates the next point 46. After locating the next point 46, process 52 is reentered at task 56 to illuminate the next point 46. If query task 64 determines that the desired number of points 46 have been illuminated and scanned, then a task 68 produces a report associated with the crystallographic characteristics of specimen 24. Preferably, the report is responsive to the confidence factors generated during crystal indexing and/or phase determination (described below). For example, the report may be configured as an image of the crystals within specimen 24, such as an orientation or grain size map, with different crystals having different imaging characteristics. FIG. 5 shows a schematic view of an exemplary report 94 configured as an image of a portion of specimen 24. The various types of reports and the significance of the different imaging characteristics will be explained in detail below. Following task 68, process 52 ends.

Figure 6:
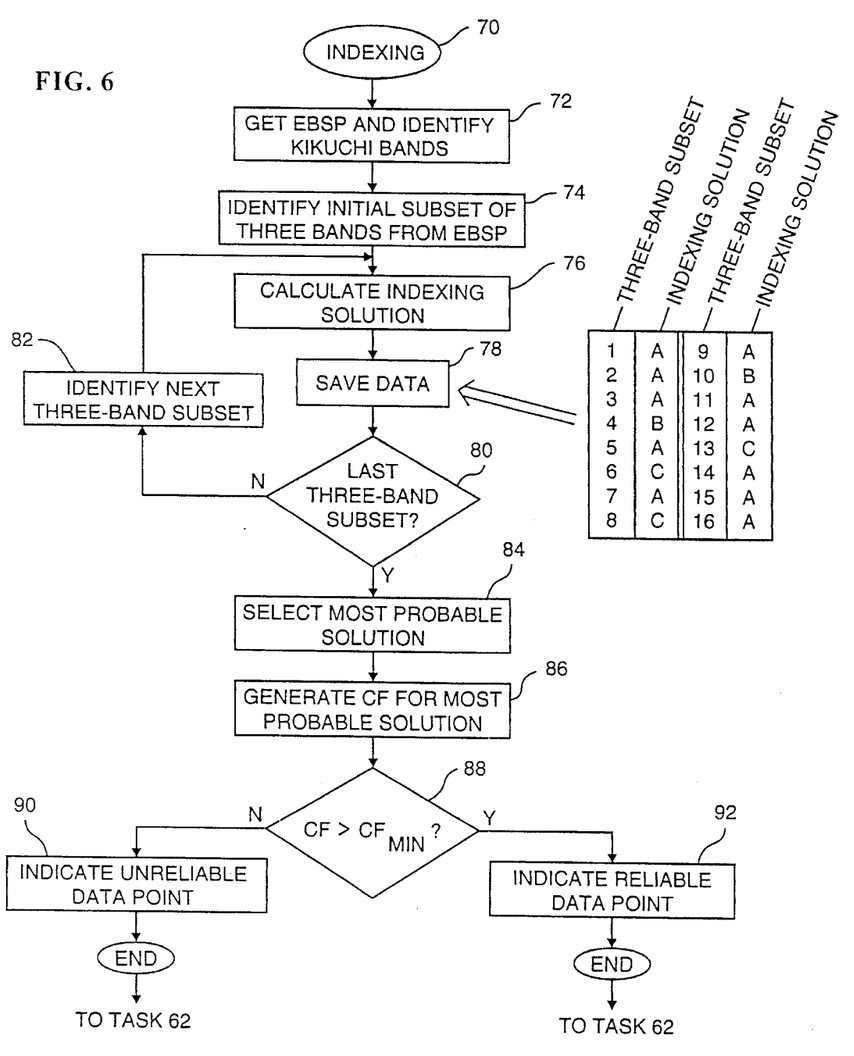
FIG. 6 is a flow diagram of an indexing process performed by the apparatus.

With reference to FIG. 6, an indexing process 70 performed by apparatus 10 is illustrated. As described briefly above, process 70 may be initiated during procedure 60 of imaging process 52. Those skilled in this art will recognize that process 70 may be performed at different times depending upon the specific application. For example, process 70 may be performed after specimen 24 has been completely scanned, rather than on a point-by-point basis. On the other hand, if processing speed is a concern, then process 70 may be performed for one crystal while task 58 collects the next EBSP.

Indexing process 70 begins with a task 72, which retrieves an EBSP for analysis, and identifies the Kikuchi bands in the EBSP. As described above in connection with imaging process 52, EBSPs are collected and digitized by image collection system 26, and stored in memory 40 of computer 38. Kikuchi bands 50 are described above in connection with FIG. 3. Task 72 utilizes well known algorithms, such as the Hough transform, to identify the Kikuchi bands. In addition, task 72 may employ other well known image enhancing techniques, such as removing the background before attempting to identify the Kikuchi bands. After an EBSP is retrieved from memory 40, a task 74 is prompted. Task 74 identifies an initial subset of three Kikuchi bands from the current EBSP. Those skilled in the art will understand that the identification of three Kikuchi bands in one EBSP provides sufficient information to index the lattice planes of the crystal under examination and that a typical EBSP includes many more than just three Kikuchi bands.

After an initial subset of three Kikuchi bands is identified, a task 76 calculates the indexing solution for the crystal associated with the current EBSP. Task 76 utilizes the Kikuchi bands identified in task 74, along with various equations, relationships, and parameters known to those skilled in the crystallography art. For example, task 76 may utilize the Bragg diffracting condition, the atomic lattice parameter for specimen 24, and/or the theoretical distance between crystal lattice planes. Each crystal type has a different set of equations and relationships which are well known to those skilled in the art and will not be described in detail herein. Following task 76, a task 78 saves the calculated data in memory 40.

After task 78, a query task 80 determines whether any other three-band subsets remain to be analyzed. Because an EBSP typically includes a number of Kikuchi bands, numerous different combinations of three bands may be analyzed during indexing process 70. For example, if seven Kikuchi bands are identified in task 72, then there are 35 different three-band combinations. The number of three-band combinations to be analyzed may be selected by the user, or a convenient default value may be utilized by process 70. If query task 80 determines that additional three-band subsets remain, then a task 82 identifies the next subset before task 76 is reentered to calculate the indexing solution again.

Tasks 76, 78, 80, and 82 create a processing loop that computes a plurality of indexing solutions utilizing different subsets of three Kikuchi bands. An exemplary data store of sixteen iterations is depicted in connection with task 78. As shown, solution A was calculated eleven times, solution B was calculated two times, and solution C was calculated three times. Thus, A, B, and C represent different mathematical models of the theoretical indexing solution for the lattice planes associated with a single crystal.

If query task 80 determines that no groups of Kikuchi bands remain to be analyzed, then a task 84 is initiated. Task 84 selects a most probable solution from the plurality of indexing solutions calculated during the processing loop defined by tasks 76, 78, 80, and 82. According to the preferred embodiment, task 84 ranks the different indexing solutions based upon their frequency of occurrence. For the exemplary indexing solutions described above, task 84 would select solution A as the most probable solution because it was calculated more frequently than any other solution. Task 84 may implement other selection criteria or utilize statistical data manipulation to select the most probable solution, and the present invention is not limited to the ranking technique described herein.

Following task 84, a task 86 generates a confidence factor (CF) for the most probable solution selected in task 84. The CF is preferably a number that indicates how reliable the selected most probable solution is. In other words, the CF indicates the likelihood that the selected indexing solution is indeed the correct solution. Rather than merely relying upon a ranking, the confidence factor is responsive to at least two of the indexing solutions. In addition, the confidence factor is preferably responsive to the total number of indexing solutions obtained during the processing loop described above. For the exemplary indexing solutions described above in connection with task 78, solution A would have a relatively high CF because it occurred eleven times and solution C (the solution with the next highest frequency of occurrence) occurred only three times. In contrast, if solution A occurred eight times and solution C occurred six times, then solution A would have a relatively low CF.

In the preferred embodiment, the CF is generated by subtracting the number of times the second most frequent solution occurred from the number of times the most probable solution occurred and dividing the difference by the total number of solutions obtained. For the above example, the CF for solution A would be generated as follows: $(11-3)/16=0.50$. Although the CF falls between zero and one in the preferred embodiment, the CF may be generated by any suitable operation that represents the probability that the most probable solution selected in task 84 is the actual solution for the crystal.

After the CF is generated in task 86, a query task 88 compares the CF to a threshold value to determine whether the CF is greater than the threshold value. The threshold value may be a fixed value based upon various parameters such as the crystal phase, or it may be defined by the user before scanning specimen 24. A user-interactive process for defining the threshold value is described in detail below. If query task 88 determines that the CF is not greater than the threshold value, then a task 90 is initiated. Task 90 indicates that the most probable indexing solution for the current crystal is unreliable. Task 90 may cause processor 42 to produce an internal flag or other indicator for the particular data point. Alternatively, task 90 may store the CF value in memory 40 for further processing. Following task 90, indexing process 70 ends. As described above, process 70 may exit into imaging process 52 at task 62.

If, however, query task 88 determines that the CF is greater than the threshold value, then a task 92 indicates that the current indexing solution is reliable. As described above in relation to task 90, task 92 may produce a flag for the data point or store the CF value for later use. Following task 92, indexing process 70 exits, preferably into task 62 of imaging process 52. The low or high CF indicators may be utilized by apparatus 10 during the production of various reports (described above in connection with task 68). For example, the most heavily shaded crystals 96 in FIG. 5 may correspond to unreliable data points and the unshaded crystals 98 may correspond to data points with unusually high CF values. Report 94 may be configured as an orientation image, a grain size map, or other representation of specimen 24 with CF data incorporated therein. Alternatively, report 94 may be configured as a confidence map that represents areas of low, high, and/or intermediate confidence. Thus, an operator may be provided with a report that indicates when to discount potentially erroneous data points during subsequent analyses.

Figure 7:
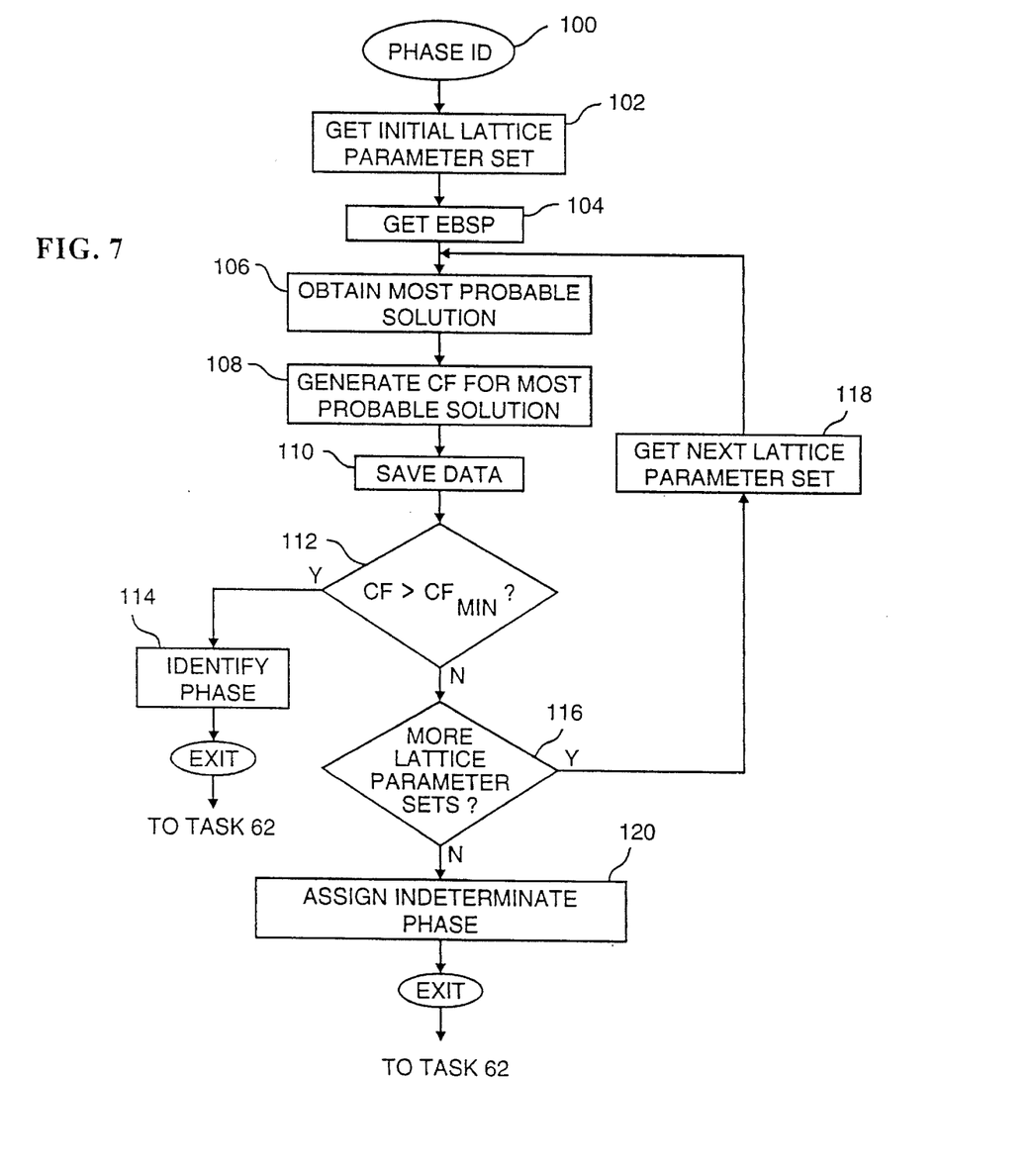
FIG. 7 is a flow diagram of a phase identification process performed by the apparatus.

Referring to FIG. 7, a phase identification process 100 performed by apparatus 10 is depicted as a flow diagram. As with indexing process 70, process 100 may be initiated during procedure 60 of imaging process 52, but process 100 may alternatively be initiated at other times depending upon the specific application. Process 100 may be performed when specimen 24 includes areas with unknown or multiple crystal phases. In addition, because crystal indexing utilizes parameters related to crystal phase, process 100 may be performed before or during indexing process 70.

Phase identification process 100 begins with a task 102, which gets an initial lattice parameter set for processing. Memory 40 preferably stores a plurality of different lattice parameter sets associated with different crystal phases. An operator may input the different lattice parameter sets prior to scanning specimen 24, or memory 40 may maintain a data store for the lattice parameter sets. The initial lattice parameter set may be designated by the operator as the most likely crystal phase for specimen 24, considering various factors known to those skilled in the art. Each lattice parameter set includes well known geometrical and mathematical relationships associated with the particular crystal phase. Once specified, these relationships allow calculation of indexing, orientation, and other crystal characteristics.

Following task 102, a task 104 gets an EBSP for processing. Task 104 may, for example, retrieve the EBSP from memory 40 after it has been digitized by image digitizer 36. After retrieving an EBSP, a task 106 obtains a most probable crystallographic solution for the crystal associated with the current EBSP. The most probable solution obtained in task 106 may be an indexing solution (as described in indexing process 70), an orientation solution, or some other crystallographic characteristic for the current crystal.

After task 106, a task 108 generates a confidence factor (CF) for the most probable solution obtained in task 106.

The above description of indexing process 70, and task 86 in particular, should be referred to for details of the generation of the CF. Briefly, the CF indicates the likelihood that the most probable solution is the correct solution for the particular crystal. Following task 108, a task 110 is performed to save the data in memory 40. Task 110 may save the solution obtained in task 106, the associated CF, and the crystal phase for the data point.

After the relevant data is stored in memory 40, a query task 112 determines whether the generated CF is greater than a threshold value. As described above in relation to task 88, the threshold value serves to distinguish relatively good data from relatively bad data. Thus, if query task 112 determines that the CF is greater than the threshold value, then the data obtained for the current crystal is considered to be reliable. When the data is reliable, a task 114 identifies the phase associated with the selected lattice parameter set for the current crystal. Because each lattice parameter set preferably includes a crystal phase parameter, task 114 may access memory 40 to identify the phase associated with the current crystal. Following task 114, phase identification process 100 ends. As described above with respect to indexing process 70, process 100 may exit into task 62 of imaging process 52.

If, however, query task 112 determines that the CF is not greater than the threshold value, then a query task 116 is prompted. Query task 116 tests whether any additional lattice parameter sets are available for analyzing the current crystal. If an unreliable solution was obtained, then the initial lattice parameter set may have been chosen incorrectly. Thus, if query task 116 determines that one or more alternate lattice parameter sets remain, then a task 118 begins. Task 118 retrieves the next lattice parameter set from memory 40, and phase identification process 100 is reentered at task 106. Process 100 employs the new lattice parameter set to recalculate a new solution and CF for the crystal.

Tasks 106, 108, 110, 112, 116, and 118 form a processing loop that analyzes the current crystal until a reliable solution is obtained. Each computational iteration utilizes a different lattice parameter set. Those skilled in this art are aware that thousands of different crystal phase variations exist. However, a skilled crystallographer can typically reduce the number of possible crystal phases for specimen 24 to a manageable number, e.g., less than about 15 different phases. As described above, the operator may initially select a limited number of available lattice parameter sets for phase identification process 100 to utilize. As such, process 100 need not perform thousands of computational loops.

If query task 116 finds that phase identification process 100 has run through all available lattice parameter sets without arriving at a reliable solution, then a task 120 begins. In other words, task 120 is initiated when the CF generated for each crystallographic solution is less than the threshold value. Task 120 assigns an indeterminate phase to the current crystal when each of the confidence factors is less than the threshold value. Task 120 may, for example, cause processor 42 to flag the current EBSP, crystal, or crystal location. Thus, rather than make unreliable crystal phase estimates, an operator may choose to ignore areas of indeterminate phase during subsequent analyses. After task 120, phase identification process 100 ends, preferably into task 62 of imaging process 52.

The phase identity, or lack thereof, may be utilized by apparatus 10 to produce a report that represents the various crystal phases within specimen 24. The production of reports is described above in connection with task 68. Report 94 in FIG. 5 may represent an exemplary crystal phase map. For example, the most heavily shaded crystals 96 may indicate crystals of a first phase and unshaded crystals 98 may indicate crystals of a second phase. Alternatively, the most heavily shaded crystals 96 may indicate crystals of an indeterminate phase. Report 94 may be configured as an independent phase map or combined with another image of specimen 24, such as a grain size map. Those skilled in the art will appreciate that apparatus 10 may generate reports corresponding to crystal orientation, specimen grain size, confidence data, and other crystallographic characteristics. In addition, such reports may be produced in a number of different formats, including printed crystallographic maps, video images, statistical tables, and the like.

Figure 8:
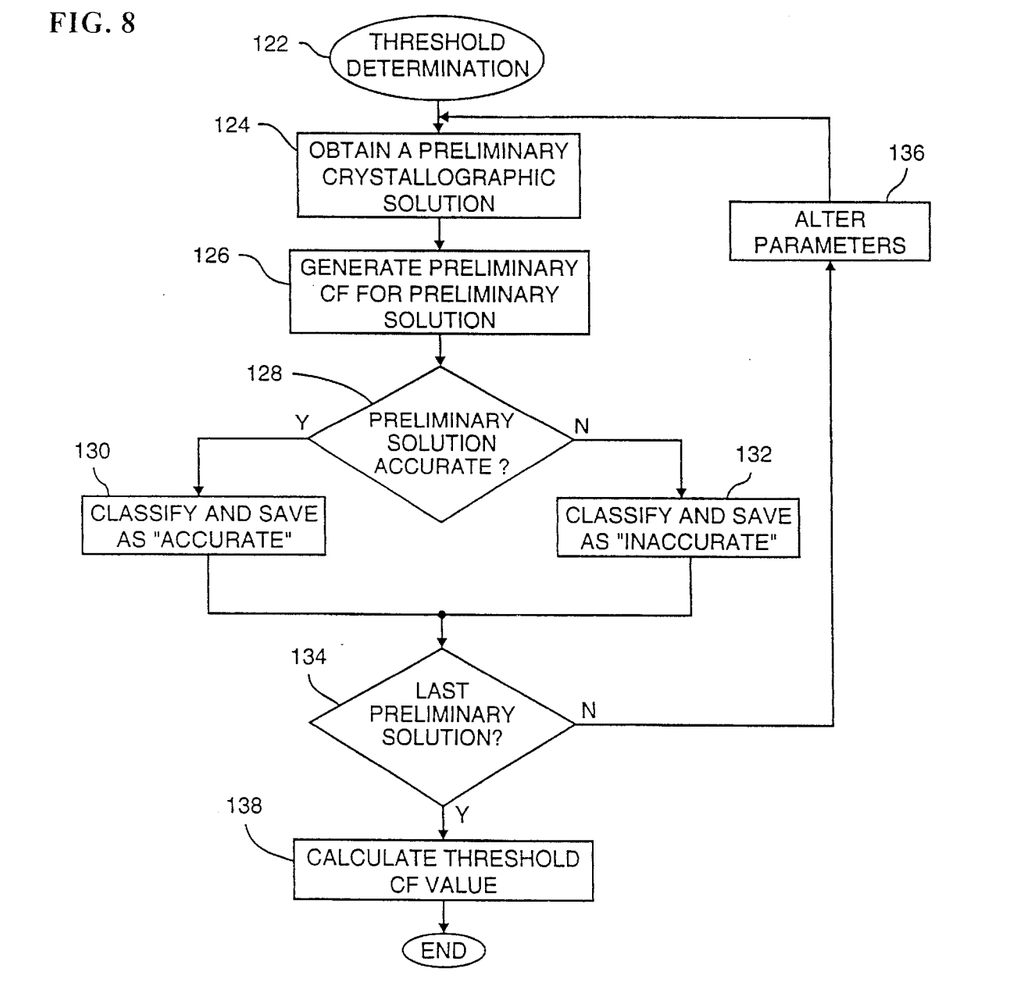
FIG. 8 is a flow diagram of a threshold determination process performed by the apparatus.

Referring now to FIG. 8, a flow diagram of a threshold determination process 122 performed by apparatus 10 is illustrated. Process 122 establishes and defines the threshold CF value utilized in indexing process 70 and phase identification process 100 (described above). Preferably, the threshold value is determined prior to scanning specimen 24 or a group of similar specimens.

Threshold determination process 122 includes with a task 124, which obtains a preliminary crystallographic solution for one or more crystals within specimen 24. The preliminary solution may be an indexing solution, an orientation solution, or other crystallographic solution. Following task 124, a task 126 generates a preliminary CF for the preliminary solution. Confidence factors and their determination were described in detail above.

After the computation of the CF, a query task 128 tests whether the preliminary solution is accurate. Task 128 may include operator intervention to determine the accuracy of the current preliminary solution. For example, an operator may use his or her know-how to analyze a display of the preliminary solution and decide whether or not the preliminary solution is accurate. If implemented in this manner, task 128 provides for an interactive determination of the threshold CF value. Alternatively, task 128 may utilize standard solutions, statistical comparisons, error detection, or other means for determining the accuracy of the preliminary solution. If query task 128 determines that the preliminary solution is accurate, then a task 130 classifies the preliminary solution as "accurate" and saves it in memory 40. On the other hand, if query task 128 determines that the preliminary solution is inaccurate, then a task 132 classifies the preliminary solution as "inaccurate" and saves it in memory 40.

Following either task 130 or task 132, a query task 134 tests whether the current preliminary solution is the last one to be analyzed. According to the preferred embodiment, threshold determination process 122 generates a statistical distribution of accurate and inaccurate solutions, along with the corresponding confidence factors. The operator may select a number of preliminary solutions to be obtained before process 122 begins or the operator may be prompted for an input during query task 134. If query task 134 finds that another preliminary solution remains to be calculated, then a task 136 is entered. Task 136 alters one or more computational parameters to allow threshold determination process 122 to calculate another preliminary solution. For example, task 136 may select a different lattice parameter set (described above). After task 136, process 122 is reentered at task 124.

If query task 134 finds that no further preliminary solutions will be obtained, then a task 138 is initiated. Task 138 calculates the threshold value such that the group of "accurate" preliminary solutions have preliminary confidence factors higher than the threshold value and the group of "inaccurate" preliminary solutions have preliminary confidence factors lower than the threshold value. In other words, task 138 analyzes the distribution of accurate and inaccurate preliminary solutions and selects the threshold CF value accordingly. Thus, for a given material sample, the threshold CF value may be interactively determined such that it correctly distinguishes reliable and unreliable crystallographic solutions during indexing process 70 and/or phase identification process 100. After task 138 calculates the threshold CF value, threshold determination process 122 ends.

In summary, the present invention provides an improved method and apparatus for indexing a crystalline specimen. An apparatus according to the present invention generates reliability data associated with an indexing or other crystallographic solution of a crystal. In addition, the present invention is capable of determining an indexing solution for a crystal without the precise knowledge of the crystal phase, and an indexing solution may be obtained for a specimen having multiple crystal phases.

The above description is of a preferred embodiment of the present invention, and the invention is not limited to the specific embodiment described and illustrated. For example, conventional electron microscope components are only generally described, and the specific apparatus may vary according to individual applications. The format of the reports and images shown and described are intended to be exemplary, and any number of different reports may be generated by an apparatus according to the present invention. In addition, the various processes and the ordering of specific tasks may be modified or changed to produce equivalent results. Furthermore, many variations and modifications will be evident to those skilled in this art, and such variations and modifications are intended to be included within the spirit and scope of the invention, as expressed in the following claims.

What is claimed is:

1. A method for determining crystallographic characteristics of a specimen, said method comprising the steps of:

(a) obtaining a plurality of indexing solutions for a crystal within said specimen;

(b) selecting a most probable solution from said plurality of indexing solutions;

(c) generating a confidence factor for said most probable solution, said confidence factor being responsive to at least two of said indexing solutions; and (d) producing a report associated with said crystal, said report being responsive to said confidence factor.

2. A method according to claim 1, further comprising the step of repeating said steps (a), (b), (c), and (d) for a plurality of crystals within said specimen.

3. A method according to claim 1, wherein said step (a) comprises the steps of:

collecting an electron backscatter diffraction pattern (EBSP) of said crystal, said EBSP having a plurality of bands;

identifying a subset of bands from said plurality of bands;

utilizing said subset of bands to calculate one of said indexing solutions; and repeating said identifying and utilizing steps for a plurality of different subsets of bands.

4. A method according to claim 1, wherein said confidence factor is responsive to the number of indexing solutions obtained in said step (a).

5. A method according to claim 1, further comprising the steps of:

defining a threshold value;

comparing said confidence factor to said threshold value;

indicating when said confidence factor is less than said threshold value; and indicating when said confidence factor is greater than said threshold value.

6. A method according to claim 5, wherein:

said report is configured as an image of said crystal;

said image has a first characteristic when said confidence factor is less than said threshold value; and said image has a second characteristic when said confidence factor is greater than said threshold value.

7. A method according to claim 5, wherein said defining step comprises the steps of:

obtaining a plurality of preliminary crystallographic solutions;

generating a preliminary confidence factor for each of said preliminary crystallographic solutions;

classifying said preliminary crystallographic solutions into a group of substantially accurate solutions and a group of substantially inaccurate solutions; and calculating said threshold value such that said group of substantially accurate solutions have preliminary confidence factors higher than said threshold value and said group of substantially inaccurate solutions have preliminary confidence factors lower than said threshold value.

8. A method according to claim 5, further comprising the steps of:

providing a first lattice parameter set, said first lattice parameter set being applied in said step (a) to obtain said plurality of indexing solutions;

providing, when said confidence factor is less than said threshold value, a second lattice parameter set associated with a second crystal phase; and repeating said steps (b), (c), and (d) utilizing said second lattice parameter set.

9. A method for determining crystallographic characteristics of a crystal within a specimen, said method comprising the steps of:

(a) providing a plurality of lattice parameter sets, each of said lattice parameter sets being associated with a different crystal phase;

(b) obtaining a plurality of most probable crystallographic solutions for said crystal, each of said most probable crystallographic solutions utilizing a different one of said lattice parameter sets;

(c) generating a confidence factor for each of said most probable crystallographic solutions;

(d) comparing each of said confidence factors to a threshold value; and (e) selecting one of said most probable crystallographic solutions in response to said comparing step.

10. A method according to claim 9, wherein, for each of said lattice parameter sets, said step (b) comprises the steps of:

collecting an electron backscatter diffraction pattern (EBSP) of said crystal, said EBSP having a plurality of bands;

identifying a subset of bands from said plurality of bands;

utilizing said subset of bands to calculate an indexing solution;

repeating said identifying and utilizing steps for a plurality of different subsets of three bands to acquire a plurality of indexing solutions; and selecting one of said plurality of indexing solutions.

11. A method according to claim 10, wherein, for each of said lattice parameter sets, said confidence factor is responsive to at least two of said plurality of indexing solutions.

12. A method according to claim 9, wherein a first confidence factor is generated for a first most probable crystallographic solution, and a second most probable crystallographic solution is obtained when said first confidence factor is less than said threshold value.

13. A method according to claim 9, further comprising the step of assigning an indeterminate phase to said crystal when each of said confidence factors is less than said threshold value.

14. A method according to claim 9, further comprising the step of repeating said steps (b), (c), (d), and (e) for a plurality of crystals within said specimen.

15. A method according to claim 9, further comprising the step of producing a report associated with said crystal, said report being responsive to said confidence factor associated with said most probable crystallographic solution selected in said step (e).

16. A method according to claim 15, wherein:

said report is configured as an image of said crystal; and said image represents said crystal phase associated with said most probable crystallographic solution selected in said step (e).

17. An apparatus for determining crystallographic characteristics of a specimen, said apparatus comprising:

an electron beam generator for generating an electron beam;

a stage for holding said specimen;

an image collection system for obtaining a diffraction image of said crystal, said diffraction image being produced by the illumination of said specimen by said electron beam; and means for processing said diffraction image to obtain a most probable indexing solution for said crystal and to generate a confidence factor associated with said most probable indexing solution, said means for processing being in data communication with said image collection system.

18. An apparatus according to claim 17, further comprising a reporting device for producing a report associated with said crystal, said reporting device being in data communication with said means for processing.

19. An apparatus according to claim 18, wherein:

said report is configured as an image of said crystal; and said image is responsive to said confidence factor.

20. An apparatus according to claim 17, wherein said means for processing is configured to determine a crystal phase of said crystal by comparing said confidence factor to a threshold value and obtaining a second indexing solution when said confidence factor is less than said threshold value.

21. An apparatus according to claim 20, further comprising a reporting device for producing a report associated with said crystal; said reporting device being in data communication with said means for processing;

said report is configured as an image of said crystal; and said image is responsive to said crystal phase.

22. An apparatus according to claim 20, further comprising a data store for storing a first lattice parameter set associated with said indexing solution and a second lattice parameter set associated with said second indexing solution.

23. An apparatus according to claim 17, wherein said diffraction image is an electron backscatter diffraction pattern (EBSP) having a plurality of bands;

said means for processing obtains said most probable indexing solution by calculating a plurality of indexing solutions and selecting one of said plurality of indexing solutions; and each of said indexing solutions is calculated by utilizing a different subset of said plurality of bands.

* * * * *